US011779730B2

(12) United States Patent
McEvoy et al.

(10) Patent No.: US 11,779,730 B2
(45) Date of Patent: Oct. 10, 2023

(54) ELONGATED MEDICAL DEVICE INTEGRITY DETERMINATION

(71) Applicant: Medtronic Vascular Galway, Galway (IE)

(72) Inventors: Francis Denis McEvoy, Laois (IE); Arthur Linnane, Dublin (IE)

(73) Assignee: Medtronic Vascular Galway, Galway (IE)

( * ) Notice: Subject to any disclaimer, the term of this patent is extended or adjusted under 35 U.S.C. 154(b) by 642 days.

(21) Appl. No.: 16/854,505

(22) Filed: Apr. 21, 2020

(65) Prior Publication Data

US 2020/0338306 A1 Oct. 29, 2020

Related U.S. Application Data

(60) Provisional application No. 62/840,067, filed on Apr. 29, 2019.

(51) Int. Cl.
*A61M 25/00* (2006.01)
*G01B 7/16* (2006.01)
*A61B 90/00* (2016.01)
*A61M 25/09* (2006.01)
*A61B 5/00* (2006.01)
(Continued)

(52) U.S. Cl.
CPC ........... *A61M 25/0054* (2013.01); *G01B 7/16* (2013.01); *A61B 5/6885* (2013.01); *A61B 90/06* (2016.02); *A61B 2017/00725* (2013.01); *A61B 2090/065* (2016.02); *A61B 2560/0223* (2013.01); *A61M 25/09* (2013.01); *A61M 2025/0002* (2013.01); *A61M 2205/0233* (2013.01); *A61M 2205/332* (2013.01); *A61M 2205/505* (2013.01); *G01M 5/0025* (2013.01); *G01M 5/0041* (2013.01)

(58) Field of Classification Search
CPC ...... A61M 25/0054; A61M 2203/0233; A61M 2205/332; A61M 2205/505; A61M 2025/0002; G01B 7/16; G01M 5/0025; G01M 5/0041; A61B 5/6885; A61B 2017/00725; A61B 2560/0223; A61B 90/06; A61B 2090/065
See application file for complete search history.

(56) References Cited

U.S. PATENT DOCUMENTS 6,236,740 B1 * 5/2001 Lee ..................... G06Q 20/40
382/305
9,107,590 B2 8/2015 Hansmann et al.
(Continued)

FOREIGN PATENT DOCUMENTS

JP 2003047654 A 2/2003

OTHER PUBLICATIONS

International Search Report and Written Opinion from counterpart International Application No. PCT/US2020/029371, dated Nov. 4, 2020, 17 pp.

*Primary Examiner* — Alexander A Mercado
*Assistant Examiner* — John M Royston
(74) *Attorney, Agent, or Firm* — Shumaker & Sieffert, P.A.

(57) ABSTRACT

In some examples, a device includes a body configured to receive an elongated medical device, and a conductive element configured to contact a touchscreen of a computing device. An amount of contact between the conductive element and the touchscreen varies based on the compressive force applied to the elongated medical device when the elongated medical device is received within the body.

14 Claims, 14 Drawing Sheets

(51) Int. Cl.
*G01M 5/00* (2006.01)
*A61B 17/00* (2006.01)

(56) References Cited

U.S. PATENT DOCUMENTS

| | | |
|---|---|---|
| 10,007,364 B2 | 6/2018 | Zimmerman et al. |
| 2016/0048225 A1* | 2/2016 | Curtis ................ G06F 3/03545 |
| | | 345/173 |
| 2017/0215970 A1* | 8/2017 | Quinn .................... A61B 90/92 |
| 2018/0224995 A1 | 8/2018 | Gui et al. |

* cited by examiner

ELONGATED MEDICAL DEVICE INTEGRITY DETERMINATION

This application claims the benefit of U.S. Provisional Application No. 62/840,067, filed on Apr. 29, 2019, and entitled, "ELONGATED MEDICAL DEVICE INTEGRITY DETERMINATION," the entire content of which is incorporated herein by reference.

TECHNICAL FIELD

This disclosure relates to medical devices.

BACKGROUND

Elongated medical devices, such as catheters and guidewires, may be advanced through vasculature of a patient during a medical procedure, such as by a clinician applying an axial pushing force or a rotational force to a portion of the elongated medical device that is outside a body of the patient. For example, a catheter defining at least one lumen may be used to deliver another medical device and/or therapeutic agent within vasculature of a patient. As another example, a guidewire may be used as a guide for placement of a larger device or prosthesis.

SUMMARY

In some examples, the present disclosure describes devices, systems, and methods for determining the integrity (e.g., actual or representative flexibility and/or stiffness properties) of an elongated medical device, which can be used, for example, to demonstrate the integrity of elongated medical devices or compare the integrity of multiple elongated medical devices. The elongated medical device can include, for example, a catheter (e.g., a guide catheter, a guide extension catheters, a microcatheter, a push wire of a catheter, or a tubular catheter body), a guidewire, or other type of elongated medical device. In some examples, a device is configured to receive an elongated medical device and transfer a compressive force applied to the elongated medical device to a force sensor, which is configured to generate an electrical signal or other output that is indicative of the amount of compressive force applied to the elongated medical device.

For example, in some examples, a device is configured to receive an elongated medical device and position the elongated medical device relative to a touchscreen of a computing device. An amount of contact between a conductive element of the device and the touchscreen varies based on the compressive force applied to the elongated medical device when the elongated medical device is received within the device. In these examples, the touchscreen may be the force sensor and the computing device may be a force-sensing device.

In examples described herein, a computing device is configured to generate and present a graphical user interface that indicates a parameter that is representative of the compressive force applied to a force sensor by an elongated medical device via the conductive element, e.g., as a numerical force value or another quantitative indication, or as a qualitative indication. For example, the computing device may determine a parameter based on the amount of contact between the conductive element and the touchscreen and generate a graphical user interface indicating the determined parameter. In some examples, a user may determine, based on the displayed graphical user interface, a minimum force required to cause the elongated medical device to bend. In addition or instead, in some examples, processing circuitry of the computing device may automatically determine the minimum force required to cause the elongated medical device to bend based on the input received via the touchscreen, the input indicating an amount of contact between a conductive element and the touchscreen, which varies as a function of the force applied to the conductive element by the elongated medical device received within the body of the force transmission device.

Clause 1: In some examples, a device comprises a body configured to receive an elongated medical device, and a conductive element configured to contact a touchscreen of a computing device, wherein an amount of contact between the conductive element and the touchscreen varies based on a compressive force applied to the elongated medical device when the elongated medical device is received within the body.

Clause 2: In some examples of the device of clause 1, the body comprises a planar surface configured to sit on the touchscreen.

Clause 3: In some examples of the device of clause 1, the conductive element is pivotably connected to the body.

Clause 4: In some examples of the device of any of clauses 1-3, the body is composed of plastic.

Clause 5: In some examples of the device of any of clauses 1-4, the body comprises a first body portion defining a first opening, and a second body portion defining a second opening aligned with the first opening, wherein the first opening and the second opening are configured to receive the medical device.

Clause 6: In some examples of the device of any of clauses 1-5, the first and second body portions are spaced apart from one another such that, in response to the compressive force, the medical device bends in a region between the first and second body portions.

Clause 7: In some examples of the device of any of clauses 1-5, the first and second body portions are spaced apart from one another such that, in response to the compressive force, the medical device bends in a region disposed on an opposite side of the first body portion from the second body portion.

Clause 8: In some examples of the device of any of clauses 1-7, the second opening is configured to receive the conductive element.

Clause 9: In some examples of the device of any of clauses 1-8, the conductive element is configured to receive an end of the elongated medical device when the elongated medical device is received within the body.

Clause 10: In some examples of the device of any of clauses 1-9, the conductive element comprises silicone rubber.

Clause 11: In some examples of the device of any of clauses 1-10, the amount of contact comprises at least one of a surface area between the touchscreen and the conductive element or an amount of force applied to the touchscreen by the conductive element.

Clause 12: In some examples, a system includes the device of clause 1 and the computing device.

Clause 13: In some examples of the system of clause 12, the computing device comprises processing circuitry configured to receive input via the touchscreen, wherein the input indicates the amount of contact between the conductive element and the touchscreen, determine a parameter based on the input, and generate a graphical user interface indicating the determined parameter.

Clause 14: In some examples of the system of clause 13, the parameter comprises a magnitude of the compressive force applied to the conductive element via the elongated medical device when the elongated medical device is received within the body.

Clause 15: In some examples of the system of clause 13, the processing circuitry is configured to determine a minimum compressive force that causes the elongated medical device to bend based on an electrical signal generated by the touchscreen based on the amount of contact between the conductive element and the touchscreen.

Clause 16: In some examples, a device comprises a touchscreen configured to receive an input from a conductive element of a medical device force transmission device, wherein the input varies as a function of a compressive force applied to the conductive element by an elongated medical device, and processing circuitry configured to determine a parameter based on the received input and generate and present a graphical user interface on the touchscreen, the graphical user interface comprising an output region configured to display the parameter.

Clause 17: In some examples of the device of clause 16, the graphical user interface further comprises an input region defining an area for receiving the input from the conductive element.

Clause 18: In some examples of the device of clauses 16 or clause 17, the parameter comprises a qualitative parameter that varies as a function of the compressive force applied to the conductive element by an elongated medical device.

Clause 19: In some examples of the device of any of clauses 16-18, the parameter comprises a quantitative parameter that varies as a function of the compressive force applied to the conductive element by an elongated medical device.

Clause 20: In some examples of the device of any of clauses 16-19, the parameter comprises a magnitude of force that changes as a function of the input.

Clause 21: In some examples of the device of any of clauses 16-20, the processing circuitry is configured to determine a minimum compressive force that causes the elongated medical device to bend based on an electrical signal generated by the touchscreen in response to the input from the conductive element.

Clause 22: In some examples of the device of clause 21, the processing circuitry is configured to determine the minimum compressive force by at least determining a peak value of the parameter.

Clause 23: In some examples, a method comprises receiving, by processing circuitry, an input via a touchscreen, wherein the input varies as a function of a compressive force applied to a conductive element by an elongated medical device; determining, by the processing circuitry and based on the input, a parameter based on the input; and generating and presenting a graphical user interface on the touchscreen, the graphical user interface comprising an output region configured to display the parameter.

Clause 24: In some examples of the method of clause 23, the graphical user interface further comprises an input region defining an area for receiving the input from the conductive element.

Clause 25: In some examples of the method of clauses 23 and 24, the parameter comprises a quantitative parameter that varies as a function of the compressive force applied to the conductive element by an elongated medical device.

Clause 26: In some examples of the method of any of clauses 23-25, the parameter comprises a qualitative parameter that varies as a function of the compressive force applied to the conductive element by an elongated medical device.

Clause 27: In some examples of the method of clause 26, the parameter comprises a magnitude of force that changes as a function of the input.

Clause 28: In some examples of the method of clause 23, the method further comprises determining, by the processing circuitry, a minimum compressive force that causes the elongated medical device to bend based on an electrical signal generated by the touchscreen in response to the input.

Clause 29: In some examples of clause 28, determining the minimum compressive force comprises determining a peak value of the parameter.

Clause 30: In some examples, a computer-readable medium comprises instructions that, when executed by processing circuitry, cause the processing circuitry to perform any of the methods of clauses 23-29.

The details of one or more aspects of the disclosure are set forth in the accompanying drawings and the description below. Other features, objects, and advantages of the disclosure will be apparent from the description and drawings, and from the claims.

DETAILED DESCRIPTION

Elongated medical devices, such as, but not limited to a catheter (or a part of a catheter, such as a push assembly or a tubular catheter body) or a guidewire, may be advanced through vasculature of a patient during a medical procedure. For example, a clinician may apply a pushing force to a proximal portion of the medical device to advance the medical device through the vasculature. Thus, the elongated medical device may be configured such that it is relatively flexible to enable the medical device to substantially conform to the curvature of the vasculature, yet stiff enough (e.g., has a sufficiently high columnar strength) to be advanced through vasculature by a pushing force applied to a proximal portion of the medical device without buckling or undesirable bending (e.g., kinking) of the medical device. In addition, in some examples, a clinician may steer an elongated medical device through the vasculature of a patient by rotating the elongated medical device. For example, the clinician may apply torque to the proximal portion of the elongated medical device (or at least a portion of the medical device that is more proximal than the distal portion implanted in the patient) in order to rotate the distal portion of the elongated medical device. Thus, in some cases, an elongated medical device has sufficient structural integrity to transmit the torque applied to a relatively proximal portion to a relatively distal portion.

For at least the reasons discussed above, the integrity (e.g., flexibility and/or stiffness) is a characteristic of an elongated medical device that may differentiate it from other elongated medical devices and may be indicative of its performance during a medical procedure. Described herein are devices and systems configured to quantitatively and/or qualitatively indicate the integrity of an elongated medical devices based on a compressive force applied to the elongated medical device, as well as devices (referred to as force transmission devices in some instances) configured to receive the elongated medical device and transmit a compressive force applied to the elongated medical device to a force sensor. The quantitative or qualitative indication of the integrity of an elongated medical device can be, for example, actual or representative flexibility and/or stiffness properties, such as, but not limited to, a numerical force value or another quantitative parameter of a compressive force that causes the elongated medical device to bend, or as a qualitative parameter that indicates a relative degree of flexibility and/or stiffness of the elongated medical device. In either the quantitative parameter example or the qualitative parameter example, the parameter determined by a computing device varies as a function of a compressive force applied to a conductive element of a force transmission device by an elongated medical device.

Figure 1:
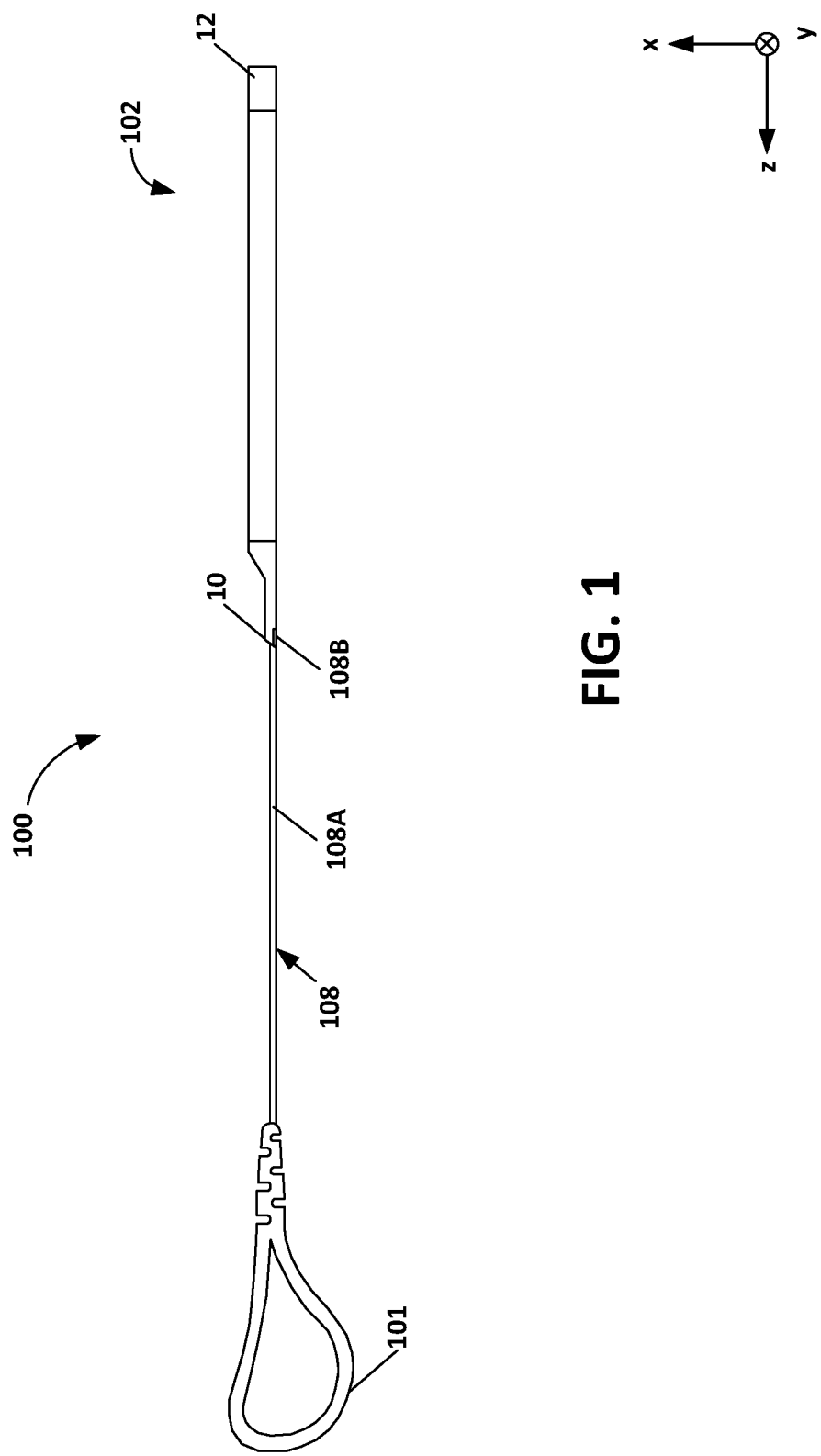
FIG. 1 is a side view of an example catheter, which includes an elongated body, a push assembly, and a handle.

FIG. 1 is a conceptual side view of an example catheter 100, which includes an elongate body 102, a push assembly 108, and a handle 101. Elongate body 102 may include an inner liner and an outer jacket (not shown). As shown in FIG. 1, elongate body 102 may define a proximal end 10 and a distal end 12.

While the description of the devices, systems, and techniques described herein primarily refer to the catheter 100 of FIG. 1, in other examples, the devices, systems, and techniques described herein may be used to determine the integrity of another elongated medical device, such as, but not limited to, a guidewire, a catheter that does not include a push assembly 108 and/or handle 101, or a polymer tube used to form a catheter or other elongated medical device. For example, example catheter 100 may include a guide catheter, a microcatheter, or any other elongated medical device.

Elongate body 102 may be a distal portion of catheter 100. Elongate body 102 defines at least one lumen through which a medical device (e.g., another catheter, guidewire, filter, stent delivery system, and the like), therapeutic agent, or other element can be introduced into vasculature or other tissue sites of a patient.

In some examples, catheter 100 may be part of an assembly that includes an outer catheter (not shown) defining a lumen through which catheter 100 may be introduced in order to access, for example, a distal target site within vasculature of a patient. Thus, at least a portion of the outer catheter may be configured to surround catheter 100. The outer catheter may define a distal opening and, in some examples, at least a portion of elongate body 102 may be configured to extend through a lumen of the outer catheter and out the distal opening of the outer catheter, e.g., to effectively extend the reach of the outer catheter within vasculature of a patient and enable delivery of devices, agents, and/or any other suitable elements to target sites that may be difficult for the outer catheter to reach. For example, elongate body 102 may be fully or partially pushed through a lumen of the outer catheter until the entire or part of elongate body 102 extends past a distal end of the outer catheter, while push assembly 108 remains fully or partially within the lumen of the outer catheter.

In some examples, catheter 100 may be configured to extend out of the distal opening of the outer catheter to extend through heavy tortuosity or calcification within a body vessel. Catheter 100 may have a smaller radial profile and may be more flexible than the outer catheter, such that it may more easily navigate through heavy tortuosity or calcification within a body vessel than the outer catheter.

Push assembly 108 is configured to enable a clinician to position elongate body 102 with respect to an outer catheter and/or with respect to patient vasculature. For example, a proximal portion of push assembly 108 may be configured to be gripped and moved by the clinician to position (e.g., advance distally or proximally, and/or rotate) elongate body 102 within vasculature of a patient. In some examples, push assembly 108 may be used to advance elongate body 102 with respect to an outer catheter to advance elongate body 102 within the outer catheter and/or extend all or a portion of elongate body 102 distal of the outer catheter to access vasculature distal to the outer catheter. Accordingly, push assembly 108 may be configured to have a relatively high integrity relative to its low profile. In other words, push assembly 108 is configured such that it may receive a relatively high magnitude compressive force (e.g., a pushing force) while resisting bending (e.g., while remaining substantially straight), despite its narrow cross-sectional area. This may enable push assembly 108 to efficiently transmit a pushing force to elongate body 102, which may in turn enable a clinician to relatively efficiently place catheter 100 at a target site within vasculature of a patient. In contrast, if push assembly 108 bends, then it may take longer and may be more difficult for a clinician to distally advance catheter 100 through vasculature, e.g., through an outer catheter or otherwise.

In some examples, elongate body 102 may include an inner liner and outer jacket that may provide multiple layers between which push assembly 108 may be inserted to attach push assembly 108 to elongate body 102. This may provide for a relatively strong attachment between push assembly 108 and elongate body 102, as well as maintain relatively smooth outer and inner surfaces of elongate body 102 at the portion of elongate body 102 attached to push assembly 108.

Push assembly 108 has a lower profile than elongate body 102, and, as a result, may occupy less space within the outer catheter lumen than elongate body 102. Thus, push assembly 108 may both facilitate pushability of the catheter through the outer catheter and/or through vasculature of a patient, while still enabling relatively large medical devices to be introduced through the outer catheter lumen to reach the lumen of the catheter.

In some examples, push assembly 108 includes an elongate member 108A (also referred to herein as a shaft) and an anchor member 108B at a distal end of elongate member 108A. Anchor member 108B is configured to facilitate attachment of elongate member 108A to elongate body 102. Anchor member 108B may be positioned at a distal end of the elongate member 108A in some examples. Elongate member 108A may be formed from any suitable material, such as, but not limited to, a metal, a polymer, or any combination thereof. For example, elongate member 108A may include a metal wire or a polymer hypotube.

In some examples described herein, systems and devices may enable a user to determine (e.g., measure) a compressive force that may be applied to push assembly 108 (e.g., elongate member 108A) without push assembly 108 bending. This compressive force may be referred to herein as a "maximum" compressive force, although it may not be an exact determination of a maximum force. The maximum compressive force may be equivalent to (or nearly equivalent to) the minimum compressive force that causes push assembly 108 to bend. Again, the minimum compressive force may not be an exact minimum compressive force that causes push assembly 108 to bend but provides an estimation of the actual minimum compressive force that is sufficient to indicate the relative integrity of the elongated medical device.

The maximum or minimum compressive force may be determined in substantially the same way for different elongated medical devices, such that it provides a representation of the integrity of the elongated medical device that can be used to compare the different elongated medical device. In some examples, systems and devices may enable a user to compare the relative flexibilities of two or more elongated medical devices, such as elongated medical devices having different configurations and/or elongated medical devices from different manufacturers. In some examples, the devices and systems described herein (e.g., including a force transmission device and a computing device) are relatively portable to enable easy transport of the devices and systems. For example, the devices and systems described herein may be small and light enough to fit in a user's clothing pocket or in a relatively small carrying case that is specially designed for the system or a standard carrying case such as a laptop bag.

Figure 2:
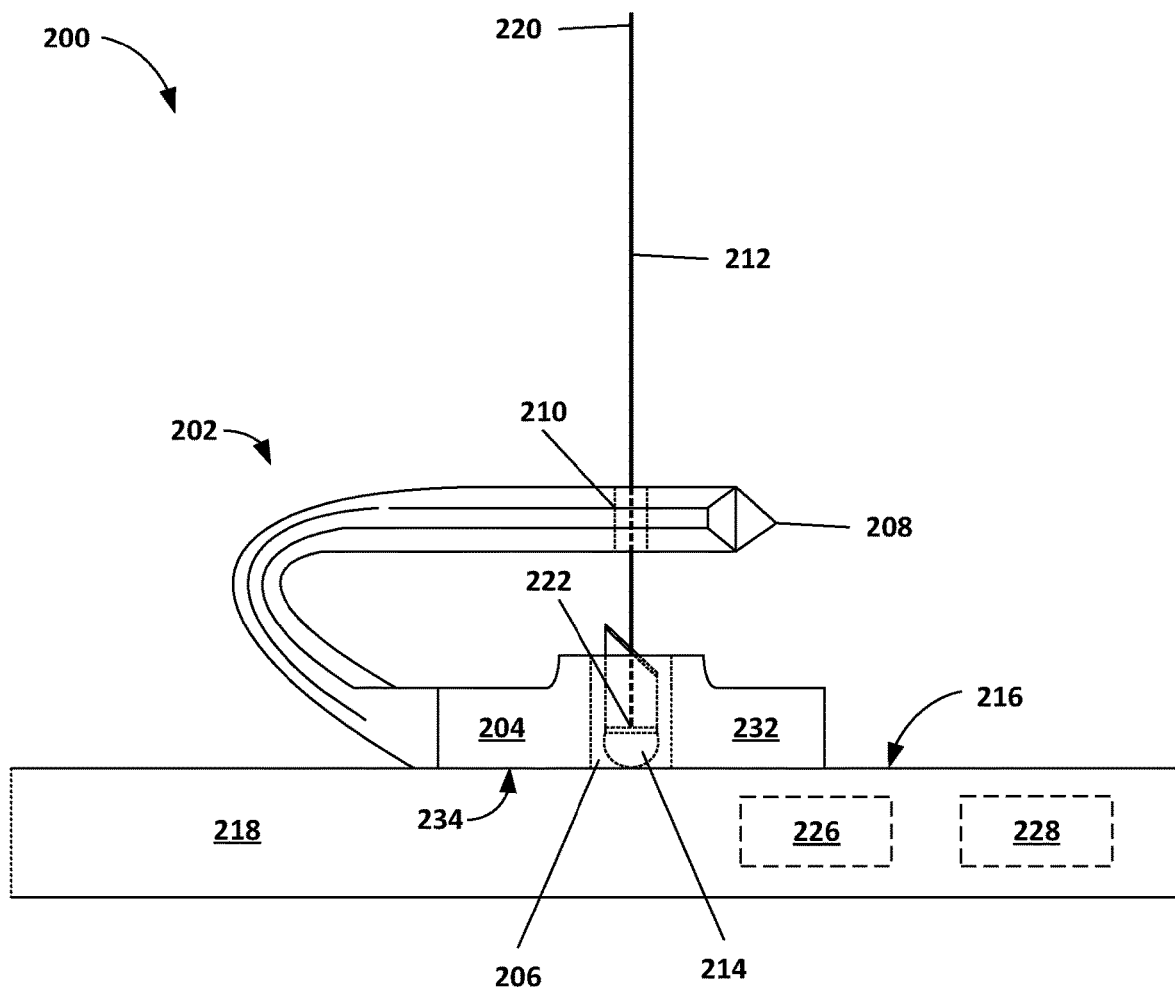
FIG. 2 is a side view of a system including an example computing device and an example device configured to receive an elongated medical device and transfer a compressive force applied to the elongated medical device to a force sensor.

FIG. 2 is a side view of an example system 200 that may be used to determine an integrity (e.g., actual or representative flexibility or stiffness parameters) of an elongated medical device, such as, but not limited to, push assembly 108 of catheter 100 (FIG. 1). As discussed in further detail below, system 200 is configured to generate a graphical user interface that provides an indication of the relative integrity of an elongated medical device. In some examples, system 200 is configured to determine a minimum amount of compressive force necessary to cause an elongated medical device to bend, or equivalently, the maximum amount of compressive force that may be applied to the elongated medical device without causing the elongated medical device to bend.

System 200 includes force-transmission device 202 (also referred to herein as a "device" in some instances) and computing device 218. Force-transmission device 202 is configured to receive an elongated medical device 212, which may be, for example, an element of push assembly 108 (FIG. 1), such as elongate member 108A, or another elongated medical device. While elongated medical device 212 is also referred to as a wire 212 herein, elongated medical device 212 may have any suitable configuration and may be formed from any suitable material, such as, but not limited to, a metal and/or a polymer. Force-transmission device 202 includes conductive element 214 and body 232 that is configured to support and align wire 212 with respect to conductive element 214.

Computing device 218 may be any suitable electronic device configured to receive input from a force sensor indicative of a force applied to wire 212 (and transmitted to the force sensor via force-transmission device 202) and generate an output based on the force, e.g., a parameter that varies based on a magnitude of the force, which can include a quantitative output (e.g., a numerical force value), a qualitative value (e.g., a color or other qualitative visual attribute that changes as a function of the amount of applied force), or a combination of a quantitative value and a qualitative output. In the example shown in FIG. 2, the force sensor is a touch-sensitive screen ("touchscreen") 216 (depicted parallel to the x-y plane in FIG. 2, where orthogonal x-y-z axes are shown in the figures for ease of description only). In other examples, however, other force sensors may be used, such as, but not limited to, a pressure transducer, a weighing scale, or a piezoelectric sensor, separate from a display screen of computing device 218. Thus, while examples described herein primarily refer to a touchscreen, the devices, systems, and techniques described herein may be used with other type of pressure sensing devices.

In the example of FIG. 2, computing device 218 is depicted as a mobile device, such as a smartphone or tablet. However, in other examples, computing device 218 may be another type of computing device. Computing device 218 includes any suitable components necessary to provide the functions described herein. In the example shown in FIG. 2, computing device 218 includes processing circuitry 226, and a computer-readable medium, such as memory 228.

In some examples, touchscreen 216 may include a capacitive touchscreen. For example, touchscreen 216 may include an embedded grid of electrically conductive strips of material, such as indium tin oxide. Touchscreen 216 may be configured to detect a physical contact with an electrically conductive element, such as a finger of a human user or conductive element 214, and generate an electrical signal indicative of the physical contact.

While capacitive touchscreens are primarily referred to herein, in other examples, touchscreen 216 may include other types of touchscreens, such as, but not limited to a resistive touchscreen configured to detect an electrical connection when a portion of a layer of touchscreen 216 (e.g., an outer layer) is depressed against another layer (e.g., an inner layer) by a compressive force applied to the resistive touchscreen by a finger or conductive element 214.

Conductive element 214 is electrically conductive and is configured to be detected by touchscreen 216 when conductive element 214 is placed in physical contact with the touch-sensitive portion of touchscreen 216. In some examples, conductive element 214 comprises an electrically conductive silicone rubber. For example, conductive element 214 may include a conductive rubber tip (or "nib"), such as that of a stylus pen.

When wire 212 is received within body 232, conductive element 214 is disposed between distal end 222 of wire 212 and touchscreen 216 of computing device 218. Conductive element 214 is configured to receive a compressive force (e.g., in the negative-z-axis direction in FIG. 2) applied to wire 212 (e.g., by a user or by a robotic arm other device), and in response, an amount of contact between conductive element 214 and touchscreen 216 changes. In this way, conductive element 214 may transfer an indication of that compressive force to a surface of touchscreen 216 by changing the amount of contact between conductive element 214 and the screen in response to the magnitude of the compressive force. For example, conductive element 214 may physically deform in response to the compressive force (e.g., flatten against touchscreen 216).

Touchscreen 216 is configured to generate an electrical signal indicative of (e.g., that changes as a function of) an amount of contact between conductive element 214 and touchscreen. Thus, the electrical signal may also be indicative of a magnitude of the compressive force applied to wire 212 when wire is received in body 232 and in contact with conductive element 214. In some examples, a greater compressive force may correspond to an increased conductive response by touchscreen 216. For example, a larger compressive force may cause a physical deformation (e.g., a flattening, on the macroscopic level, of a rounded tip) of conductive element 214, creating a larger area of contact between conductive element 214 and touchscreen 216. As another example, a larger compressive force may cause an increase in electrical conductance between conductive element 214 and touchscreen 216, due to an increased number of electrical connections at the microscopic level.

Computing device 218 is configured to receive data indicative of the electrical signal from touchscreen 216 and determine a parameter based on the data (e.g., an approximate magnitude of the compressive force) based on the electrical signal. In some examples, computing device 218 is configured to generate and present a graphical user interface (GUI) via touchscreen 216, the GUI indicating the determined parameter (e.g., an example of which is discussed with reference to FIG. 9). The determined parameter can be a quantitative value (e.g., a numerical value of the magnitude of force) or a qualitative value (e.g., a color or depth of color, or other visual indication) that varies based on the amount of contact between the conductive element and the touchscreen.

Figure 3:
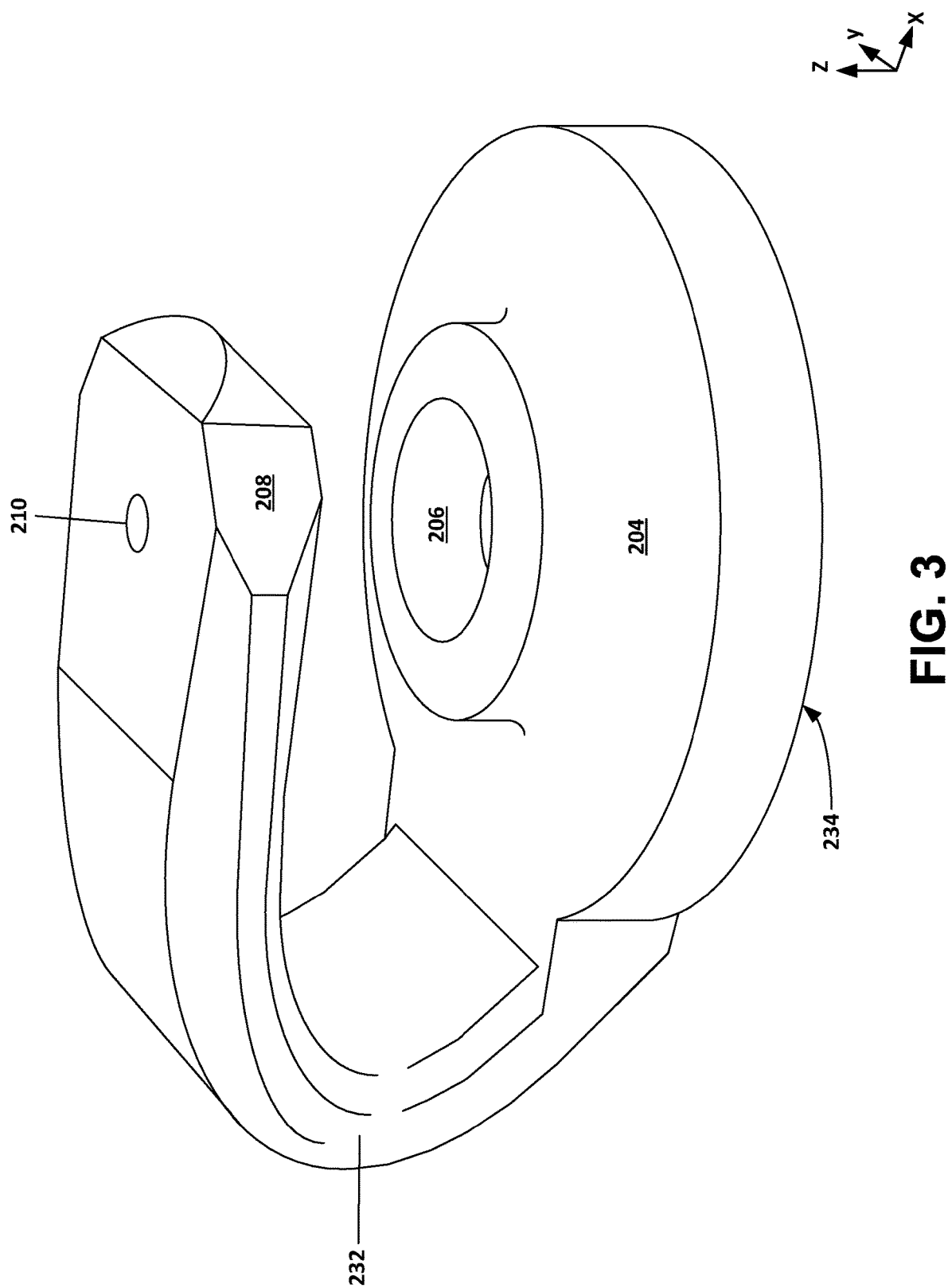
FIG. 3 is a perspective view of the device of the system depicted in FIG. 2.

FIG. 3 is a perspective view of body 232 of device 202 of the system depicted in FIG. 2. In some examples, body 232 may be configured to support an elongated medical device, such as push assembly 108 (FIG. 1) or wire 212 (FIG. 2). Body 232 may be relatively lightweight and portable as compared to some other integrity-testing devices. For example, body 232 may be made of plastic, such as a molded plastic, and may have at least one dimension that is smaller than a mobile device to enable body 232 to sit on a touchscreen of the mobile device. Body 232 may include a single piece of material, or multiple pieces of material fused, welded, or otherwise connected together.

In some examples, base 204 is configured to rest on a touchscreen 216 of computing device 218 (FIG. 2). For example, base 204 may include a planar undersurface 234 configured to align with and sit directly on or indirectly on a planar surface of touchscreen 216. In some examples, base 204 may include a relatively high-friction material on undersurface 234 to increase the static friction between base 204 and touchscreen 216 (e.g., a glass or plastic surface of touchscreen 216). Thus, the relatively high-friction material may help minimize movement between base 204 and touchscreen 216, e.g., during the application of compressive force to wire 212 received within body 232. The relatively high friction material can be, for example, a coating applied to undersurface 234, a material integrated into a material of base 204, a surface treatment of underside 234 of body 232, or a separate friction element applied (e.g., a non-conductive rubber and/or silicone) to undersurface 234.

In the example shown in FIG. 3, body 232 includes base 204 and arm 208 extending from base 204. Base 204 and arm 208 are configured to support and align wire 212 with respect to touchscreen 216. For example, base 204 may be configured to support and retain distal end 222 of wire 212, and arm 208 may be configured to support wire 212 at a second point along its length. In some examples, arm 208 may be spaced far enough from base 204 to provide stability for wire 212, but close enough to base 204 such that a majority of the length of wire 212 extends above arm 208 in the z-axis direction when wire 212 is received within body 232. For example, arm 208 may be spaced approximately 10 millimeters (e.g., 10 millimeters to the extent permitted by manufacturing tolerances) from base 204 for a wire 212 having a length of approximately 150 millimeters. In other examples, arm 208 may be spaced relatively far from base 204, such that a majority of wire 212 is disposed within a region between base 204 and arm 208 when wire 212 is received within body 232. The distance between base 204 and arm 208, as well as the length of wire 212 (measured from proximal to distal ends) may dictate where wire 212 bends in response to the compressive force applied to wire 212 in a direction towards touchscreen 216.

Body 232 is configured to hold wire 212 (or another elongated medical device) relative to touchscreen 216, e.g., in a substantially fixed x-y position (to the extent base 204 remains in place relative to touchscreen 216) while a compressive force is being applied to wire 212. For example, in some examples, base 204 defines base opening 206, which is configured to receive distal end 222 of wire 212, and arm 208 defines arm opening 210, through which distal end 222 of wire 212 may be received to reach base opening 206. For example, arm opening may have a diameter approximately two to three times as wide as wire 212 (e.g., as a widest cross-sectional dimension of wire 212, such as a diameter of wire 212 in examples in which wire 212 has a circular cross-section). Arm opening 210 may be substantially aligned (e.g., sharing a common central axis as permitted by manufacturing tolerances) with base opening 206, so as to receive a straight wire 212 (when no compressive force is being applied to wire 212). When wire 212 is received in body 232 such that it extends through both base opening 206 and arm opening 210, body 232 supports and aligns wire 212, for example, along the z-axis depicted in FIG. 3.

In some examples, base opening 206 may also be configured (e.g., sized and shaped) to receive and surround conductive element 214 (FIG. 2), such that when wire 212 extends through both base opening 206 and arm opening 210, conductive element 214 is positioned between distal end 222 of wire 212 and touchscreen 216. In other examples, however, conductive element 214 can be positioned distal to base opening 206 (i.e., such that base opening 206 is between conductive element 214 and arm opening 210).

Figure 4:
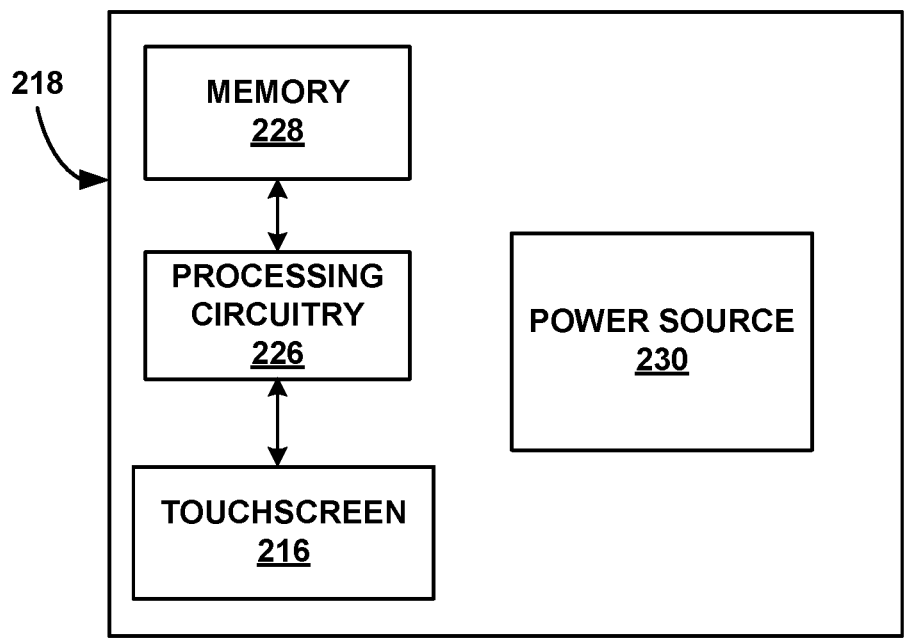
FIG. 4 is a block diagram of an example computing device.

FIG. 4 is a block diagram of an example computing device that is configured to determine a parameter based on data indicating an amount of contact between conductive element 214 and touchscreen 216 and generate and present a graphical user interface on touchscreen 216 indicating the parameter. In the example shown in FIG. 4, computing device 218 includes touchscreen 216, processing circuitry 226, memory 228, and power source 230.

Touchscreen 216 is configured to receive an input from conductive element 214 indicative of a compressive force applied to conductive element 214 by wire 212 (e.g., as applied to the wire from a user). Touchscreen 216 is configured to generate a signal indicative of the input, e.g., an electrical signal that varies in at least one characteristic (e.g., amplitude or frequency) as a function of the amount of contact between conductive element 214 and touchscreen 216, and provide the electrical signal to processor 226. As discussed above, touchscreen 216 can be a capacitive touchscreen, configured to detect a change in its internal electric field, or a resistive touchscreen, configured to detect a contact between two internal conductive layers. In other examples, computing device 218 includes a non-touchscreen display and a separate force sensor. In these examples, the force sensor is configured to receive the input from conductive element 214

Processing circuitry 226 is configured to receive the electrical signal from touchscreen 216 indicative of a compressive force applied to conductive element 214 via wire 212 and determine a parameter based on the electrical signal. In some examples, the parameter can be, for example, a numerical value of the magnitude of the compressive force, a graphical representation of the magnitude, or a qualitative indication of the compressive force, such as a relative color scale.

For example, processing circuitry 226 may be configured to execute an algorithm to convert the electrical signal generated by touchscreen 216 into an approximate magnitude of the compressive force.

In some examples, processing circuitry 226 may store the determined parameter in memory 228. Memory 228 may comprise any suitable medium, such as random-access memory (RAM), read-only memory (ROM), programmable read-only memory (PROM), erasable programmable read-only memory (EPROM), electronically erasable programmable read-only memory (EEPROM), flash memory, comprising executable instructions for causing processing circuitry 226 to perform the actions attributed to it. For example, memory 228 may store instructions thereon, that, when executed by processing circuitry 226, cause processing circuitry 226 to determine a magnitude of a compressive force applied to wire 212 based on an electrical signal received from touchscreen 216. In some examples, memory 228 may encode a lookup table storing a set of values of magnitudes of compressive forces, as well as a set of respective electrical signals that may be received from touchscreen 216.

Figure 5:
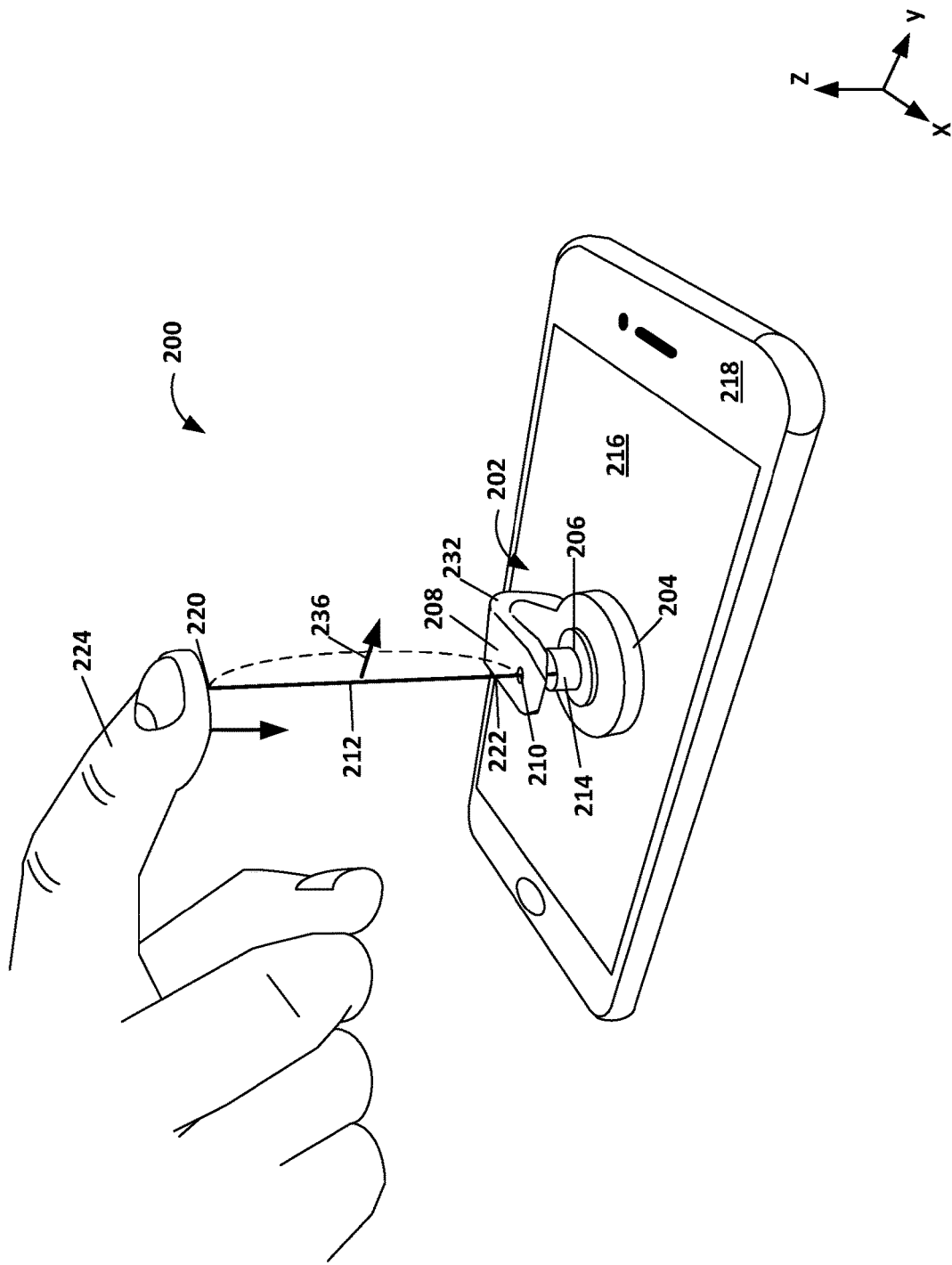
FIG. 5 is a perspective view of the system of FIG. 2 and illustrates a user applying a compressive force to an elongated medical device received within the device.

FIG. 5 is a perspective view of the system 200 and illustrates a user applying a compressive force to wire 212 received by device 202. FIG. 5 illustrates base 204 of body 232 of device 202 placed on touchscreen 216 (e.g., on an outer surface) of computing device 218. A distal end 222 of wire 212 has been introduced through arm opening 210 and base opening 206, until distal end 222 contacts conductive element 214, such that it extends away from a major surface of touchscreen 216 in the z-axis direction. In examples in which wire 212 is substantially straight in an "at rest" position in which user 224 is not applying a compressive force to wire 212, wire 212 may be substantially parallel to the z-axis (e.g., parallel but for manufacturing tolerances that result in a non-straight wire 212).

User 224 may apply a compressive force (such as with a finger, in the negative-z-axis direction) to proximal end 220 of wire 212 or to a portion of wire 212 that is between proximal end 220 and arm 208 of device 202. Once user 224 has applied a sufficient compressive force, wire 212 will bend, such as in the x-y plane (indicated in FIG. 4 by arrow 236 at the center of wire 212, pointing in the y-axis direction). For example, arm 208 and base 204 may be spaced relatively close together, such that wire 212 tends to bend in a region above (in the z-axis direction) arm 208. In other words, the majority of the length of wire 212 may be disposed in a region proximal to user 224 relative to arm 208, providing space for wire 212 to bend. In other examples, arm 208 and base 204 may be spaced relatively far apart, such that wire 212 tends to bend in a region between arm 208 and base 204. In other words, the majority of the length of wire 212 may be disposed in a region between arm 208 and base 204, providing space for wire 212 to bend.

In response to the compressive force applied to wire 212 by user 224, conductive element 214 may deform, increasing an amount of contact with touchscreen 216. For example, the physical contact between conductive element 214 and touchscreen 216 may increase in surface area and/or pressure as a function of the compressive force applied to wire 212. Touchscreen 216 is configured to output an electrical signal indicating the amount (e.g., area and/or pressure) of the contact with conductive element 214. Thus, the electrical signal output by touchscreen 216 may also be indicative of a compressive force applied to conductive element 214 via wire 212.

Processing circuitry 226 of computing device 218 receives the electrical signal from touchscreen 216 and determines a parameter based on the electrical signal. For example, processing circuitry 226 may determine an approximate measurement of the magnitude of the compressive force based on the electrical signal, such as by executing an algorithm relating the data from the touchscreen to a respective magnitude of a compressive force. In other examples, processing circuitry 226 may be configured to retrieve an entry from a lookup table stored by memory 228 relating electrical signals (or specific signal characteristics) generated by touchscreen 216 to a respective magnitude of a compressive force. Processing circuitry 226 may then generate and present a GUI on touchscreen 216, the GUI comprising an output region that displays the determined parameter indicative of the compressive force.

In some examples, user 224 may visually determine (e.g., estimate) the magnitude of the applied compressive force at the point at which wire 212 bends, which may be the minimum compressive force that causes wire 212 to bend or the maximum compressive force that wire 212 can withstand before bending, as discussed above. For example, processing circuitry 226 may update the GUI at a rate (e.g., multiple times per second) that enables the GUI to reflect an amount of compressive force currently being applied to wire 212. User 224 may subjectively estimate the first appearance of a curvature along wire 212, and observe the force measurement presented on the GUI at or near that point in time to determine the magnitude of the applied compressive force at the point at which wire 212 bends.

In addition to or instead of user 224 determining the magnitude of the applied compressive force at the point at which wire 212 bends based on the force information displayed via the GUI, in some examples, processing circuitry 226 is configured to determine the applied compressive force at which wire 212 bends, which may be indicative of the integrity of wire 212. For example, at the point at which the compressive force applied to wire 212 causes the wire to bend, the energy applied to wire 212 may be redirected into deformation (bending) of wire 212, rather than into deformation of conductive element 214 against touchscreen 216, and accordingly, the amount of contact between conductive element 214 and touchscreen 216 may temporarily stop increasing or otherwise changing in response to the increased force. Accordingly, in some examples, processing circuitry 226 may be configured to receive an electrical signal from touchscreen 216, where a signal parameter of the electrical signal changes as a function of the contact between conductive element 214 and touchscreen 216, and determine the point at which a signal parameter of the electrical signal stops changing, and determine the magnitude of the compressive force at that point. For example, processing circuitry 226 may be configured to determine a peak of magnitude of the electrical signal and determine that peak to be the magnitude of the applied compressive force at the point at which wire 212 bends.

Although force-transmission device 202 shown in FIGS. 2, 3, and 5 is configured to hold wire 212 generally transverse (e.g., perpendicular) to a major surface of touchscreen 216, in other examples, a force-transmission device can be configured to hold wire 212 generally parallel to major surface of touchscreen 216. This may help better simulate the orientation of wire 212 during a medical procedure and provide a user with a more "real world" setting in which the relative integrity of wire 212 is determined.

Figure 6:
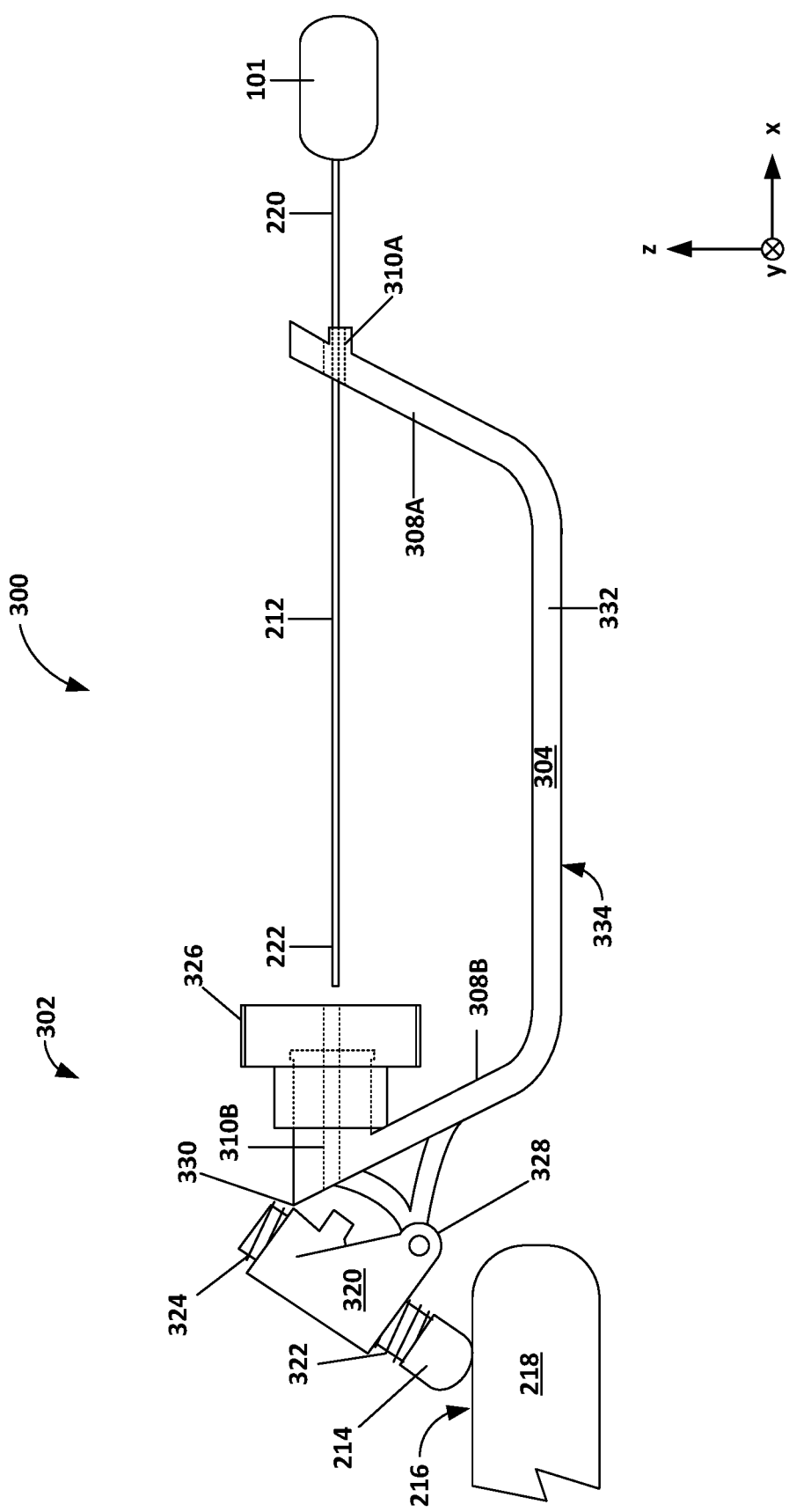
FIG. 6 is a side view of a system including another example device configured to receive an elongated medical device and transfer a compressive force applied to the elongated medical device to a force sensor.

FIG. 6 is a side view of a system 300 including another example force-transmission device configured to receive an elongated medical device and transfer a compressive force applied to the elongated medical device to a force-sensing device. System 300 includes force-transmission device 302 (detailed further with respect to FIG. 7, below) and computing device 218. In the example depicted in FIG. 6, force-transmission device 302 is configured such that, unlike in the previous example, base 304 of body 332 does not rest on touchscreen 216. Because conductive element 214 is the only object in physical contact with touchscreen 216, the example system of FIG. 6 may provide more accurate measurements of a compressive force compared to system 200 shown in FIG. 1. However, with either system, consistent methodology in obtaining data may be sufficient to account for touchscreen-related error.

Force-transmission device 302 includes body 332 and conductive element 214. Body 332 is configured to receive an elongated medical device (e.g., wire 212) and hold the elongated medical device 212 relative to touchscreen 216. Body 332 is further configured to transfer (e.g., redirect) a compressive force applied to wire 212 (e.g., in the negative-x-axis direction) when wire 212 is received in body 332 to conductive element 214 (e.g., in the negative-z-axis direction).

Figure 7:
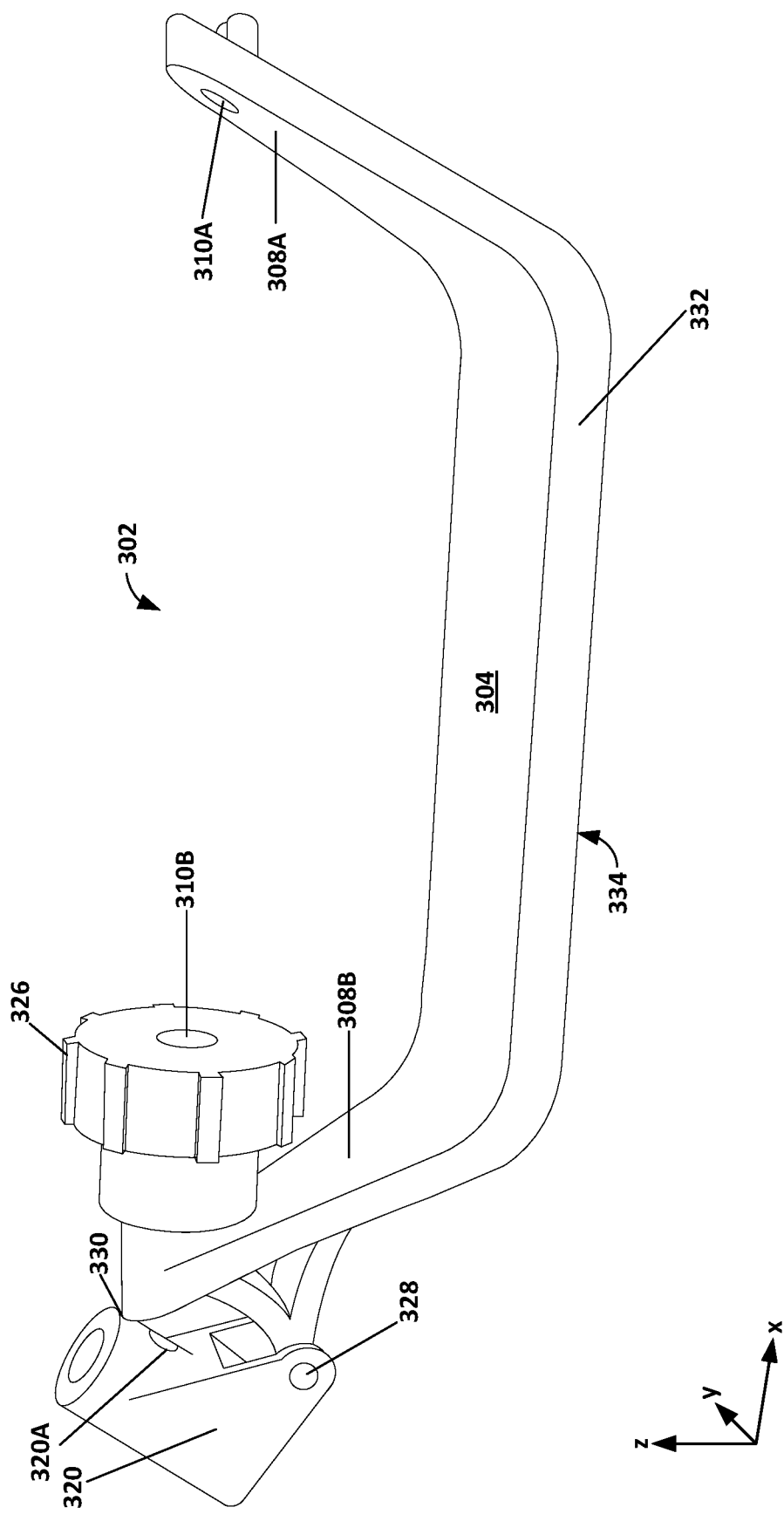
FIG. 7 is a perspective view depicting the device of the system depicted in FIG. 6.

FIG. 7 is a perspective view of body 332 of force-transmission device 302 of the system 300. Body 332 may be made from any suitable material, such as, but not limited to plastic, such as a molded plastic. Body 332 includes base 304, proximal arm 308A, distal arm 308B, and lever 320.

Base 304 may include a relatively flat (e.g., planar) surface 334 configured to be aligned (e.g., in the x-y plane) with computing device 218 (FIG. 5). For example, when in use, base 304 may be placed adjacent to computing device 218, such as on top of a common planar surface. In some examples, base 304 includes planar surface 334, configured to contact and rest on a common planar surface with computing device 218. In some examples, 334 may include a friction-enhancing element, such as a rubber coating, to reduce or prevent body 332 from moving or slipping (in the x-y plane) with respect to computing device 218.

Proximal and distal arms 308A, 308B are configured to receive and support respective ends of wire 212. For example, proximal arm 308A may define proximal arm opening 310A configured to receive and support proximal end 220 of wire 212, and distal arm 308B may define distal arm opening 310B configured to receive and support distal end 222 of wire 212. Distal arm opening 310B may be substantially aligned (e.g., sharing a common central axis) with proximal arm opening 310A, so that a substantially straight wire 212 may be relatively easily extend through both openings 310A, 310B. Proximal arm 308A may be spaced apart from distal arm 308B such that, when wire 212 is received within body 332, a majority of the length of wire 212 is disposed in a region between the two arms, such that wire 212 has space to bend within this region. Proximal arm opening 310A and distal arm opening 310B may be a common distance from base 304 (in the z-axis direction) such that wire 212 is disposed parallel to touchscreen 216 when wire 212 is received within body 332. Proximal arm opening 310A may be, for example, approximately 10 centimeters (about four inches)(in the x-axis direction) from distal arm opening 310B.

Lever 320 defines recess 320A configured to receive distal end 222 of wire 212. For example, recess 320A may be aligned with distal arm opening 310B, such that when wire 212 in a substantially linear configuration is inserted through distal arm opening 310B, wire 212 also extends through recess 320A. Recess 320A is not a through-hole, and defines a predetermined region for wire 212 to engage with lever 320 to cause lever 320 to move in response to a compressive force applied to wire 212. In other examples, lever 320 may not define recess 320A, but, rather, distal end 222 of wire 212 may engage with an outer surface of lever 320.

Lever 320 includes an element configured to redirect a compressive force from wire 212, for example, from the negative-x-axis direction into the negative-z-axis direction. For example, lever 320 may be rotatably or pivotably connected, via hinge 328, to distal arm 308B, such that lever 320 rotates toward the negative-z-axis direction when wire 212 contacts lever 320 in the negative-x-axis direction. In some examples, lever 320 is configured to receive conductive element 214. However, in other examples, lever 320 and conductive element 214 may be the same component, such that conductive element 214 is pivotably connected to distal arm 308B, and is configured to directly receive distal end 222 of wire 212.

In some examples, lever 320 includes lower set screw 322 and upper set screw 324 (depicted in FIG. 6). Lower set screw 322 includes a threaded element configured to allow a user to adjust the height of conductive element 214 with respect to touchscreen 216 of computing device 218. For example, lower set screw 322 may be rotated so as to partially enter or exit lever 320 such that, when conductive element 214 is resting on top of touchscreen 216, lever 320 is in physical contact with distal arm 308B at contact point 330. Once lower set screw 322 has been adjusted to the proper height, upper set screw 324 may be inserted into lever 320 to secure lower set screw 322 in place.

In some examples, device 302 includes Tuohy-Borst Adaptor 326, configured to receive and support distal end 222 of wire 212. However, other examples of device 302 may not include Tuohy-Borst Adaptor 326.

Figure 8:
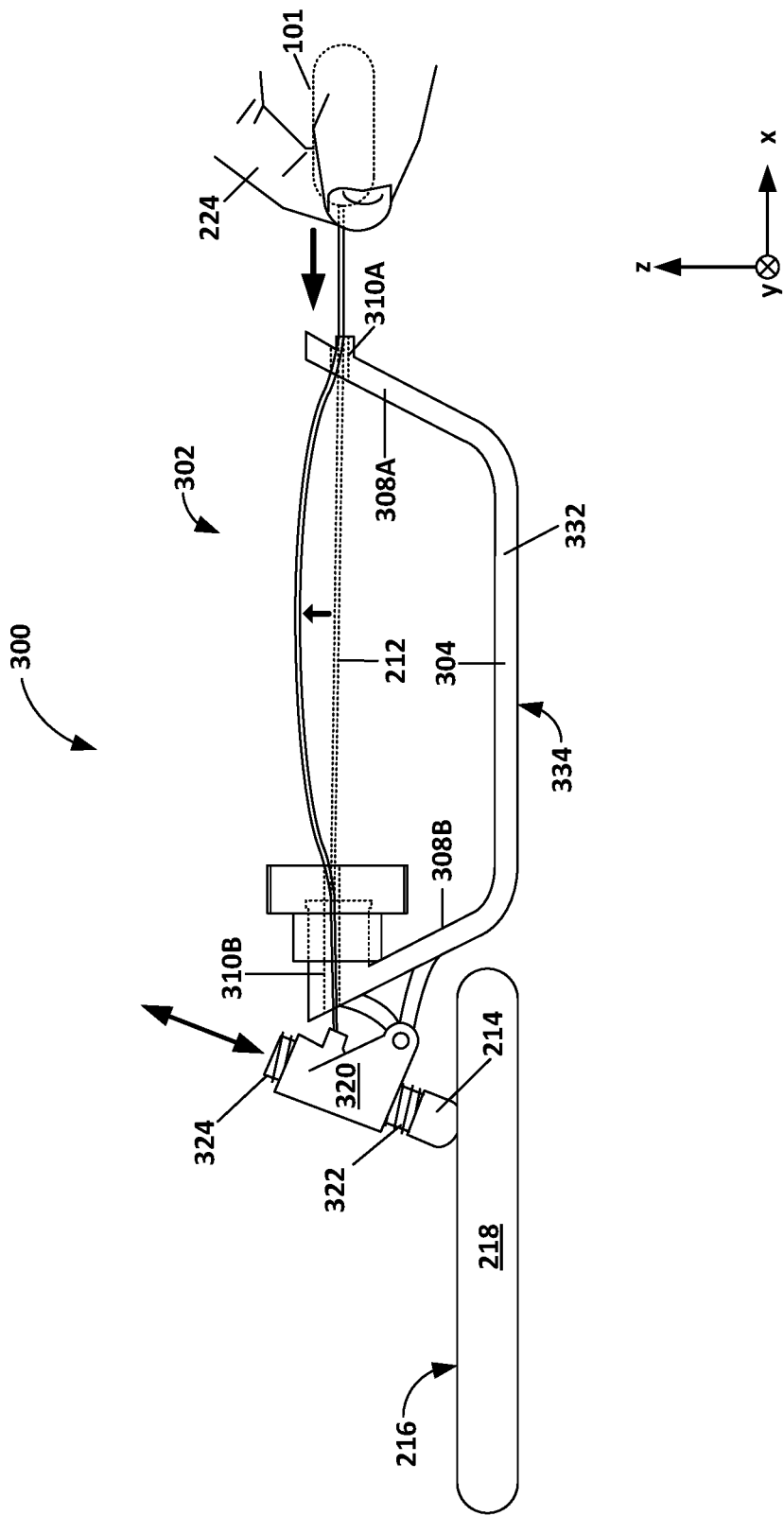
FIG. 8 is a side view of the system of FIG. 6 and illustrates a user applying a compressive force to an elongated medical device received within the device.

FIG. 8 is a side view of the system of FIG. 6 and illustrates a user applying a compressive force to an elongated medical device 212 received within the force-transmission device 302. User 224 removes upper set screw 324 to unlock lower set screw 322. User 224 places base 304 of device 302 adjacent to computing device 218, such that conductive element 214 is above touchscreen 216 (e.g., in the positive z-axis direction). User 224 adjusts lower set screw 322 to a height at which conductive element 214 contacts touchscreen 216, and lever 320 contacts distal arm 308B at contact point 330. User 224 re-inserts upper set screw 324 until upper set screw 324 contacts lower set screw 322 to secure lower set screw 322 in place.

User 224 inserts distal end 222 of wire 212 through proximal arm opening 310A and distal arm opening 310B, until distal end 222 contacts lever 320. User 224 applies a compressive force (such as with one or more fingers, in the negative-x-axis direction) to handle 101 at proximal end 220 of wire 212. Lever 320 rotates in response to the contact from wire 212, redirecting the compressive force from the negative-x-axis direction into the negative-z-axis direction, and onto touchscreen 216.

In response to the compressive force, conductive element 214 may deform, increasing an amount of contact with touchscreen 216. For example, the physical contact between conductive element 214 and touchscreen 216 may increase in both area and/or pressure as a function of the compressive force applied to wire 212. Touchscreen 216 is configured to output an electrical signal, e.g., data, indicating the amount (e.g., area and/or pressure) of contact with conductive element 214.

Computing device 218 receives the data from touchscreen 216 and determines an approximate measurement of the magnitude of the compressive force based on the data. For example, computing device 218 may be configured to execute an algorithm relating the data from the touchscreen to a respective magnitude of a compressive force. In other examples, computing device 218 may be configured to retrieve an entry from a lookup table relating the data from the touchscreen to a respective magnitude of a compressive force. Computing device may then output the measurement via a GUI displayed on touchscreen 216.

Once user 224 has applied a sufficient compressive force, wire 212 will bend, such as in the y-z plane between proximal arm 308A and distal arm 308B (indicated in FIG. 7 by the thick black arrow pointing in the z-axis direction).

In some examples, user 224 may visually determine (e.g., estimate) the magnitude of the applied compressive force at the point at which wire 212 bends. For example, the GUI may continuously update to reflect the amount of compressive force currently being applied to wire 212. User 224 may subjectively estimate the first appearance of a curvature along wire 212, and observe the force measurement on the GUI at that point.

In other examples, computing device 218 may be configured to quantitatively estimate and store the minimum applied compressive force required for wire 212 to bend. For example, at the point at which the compressive force applied to wire 212 causes the wire to bend, the energy applied to wire 212 may be redirected into deformation (bending) of wire 212, rather than into deformation of conductive element 214 against touchscreen 216, and accordingly, the amount of contact between conductive element 214 and touchscreen 216 may temporarily stop increasing or otherwise changing in response to the increased force. Accordingly, computing device 218 may be configured to monitor the signal received from touchscreen 216 and determine the point at which the signal stops changing, and determine the magnitude of the compressive force at that point.

Figure 9:
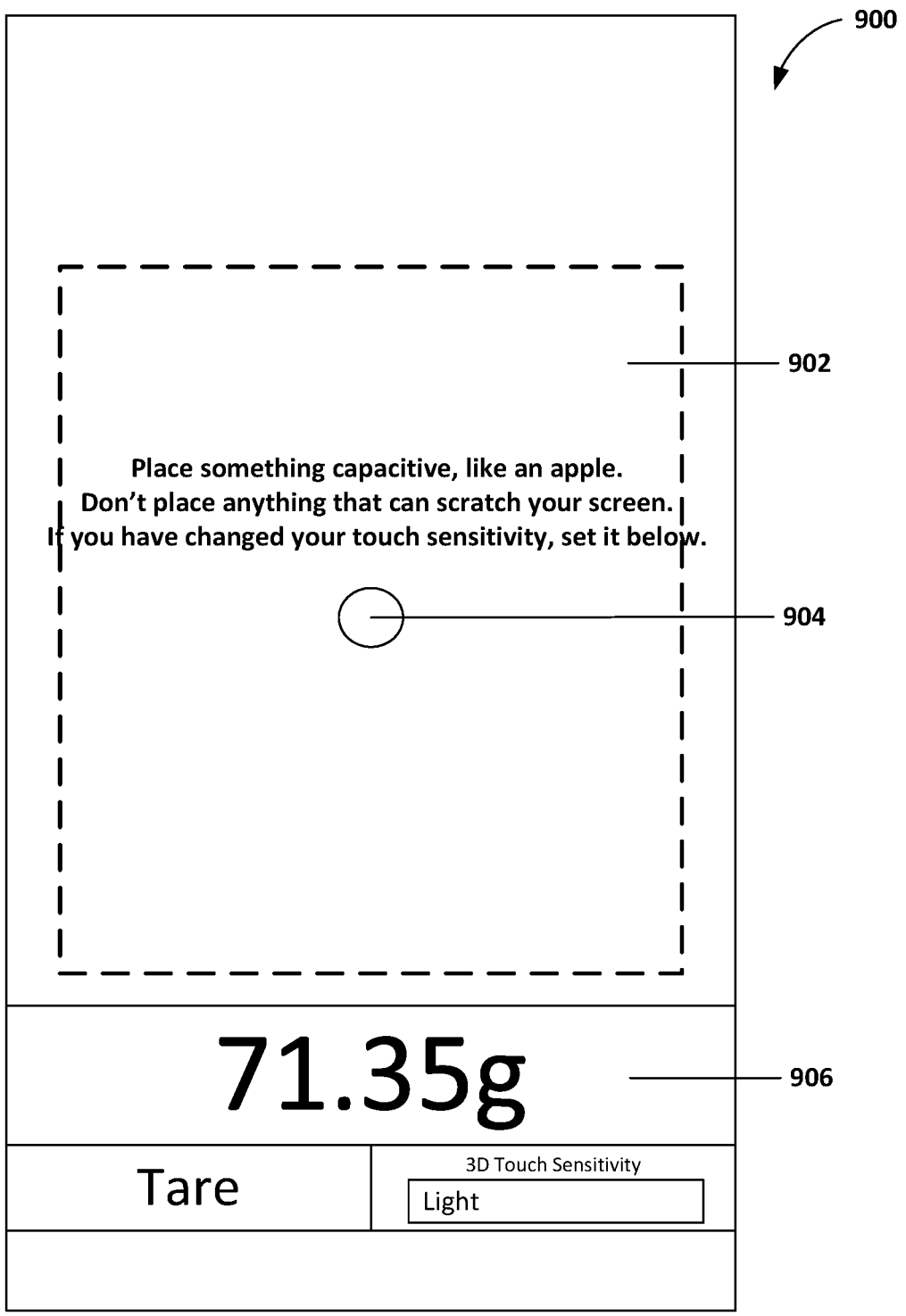
FIG. 9 illustrates an example graphical user interface (GUI) that may be generated and displayed by a computing device of any of the systems described herein.

FIG. 9 illustrates an example GUI 900 that may be generated and displayed by a computing device of any of the systems described herein. For example, processing circuitry 226 may generate and present GUI 900 on touchscreen 216 of computing device 218 (FIG. 4). GUI 900 includes input region 902 and output region 906. Input region 902 graphically indicates an area on which a user may place surface 234 of base 204 of body 232 of device 202 (FIG. 2). For example, a user may place base 204 of device 202 within input region 902 such that conductive element 214 is aligned with contact point 904. In other examples, user may place device 202 anywhere within input region 902, or use contact point 904 as a visual guide for placement. Touchscreen 216 may detect an electrical signal from contact point 904 when conductive element 214 contacts contact point 904.

Output region 906 includes an area configured to display an indication of a parameter indicative of compressive force, based on the amount of contact between the conductive element 214 and touchscreen 216, determined by processing circuitry 226. For example, processing circuitry 226 may determine an approximate magnitude of a compressive force based on an electrical signal generated by touchscreen 216 based on input received via contact point 904 of input region 902, and GUI 900 may display the approximate magnitude as a numerical value within output region 906. For example, GUI 900 may display the numerical value of the compressive force in units of Newtons (N) or Earth-gravities (g) within output region 906. In some examples, GUI 900 may display a previously determined parameter, such as a force magnitude, for comparison with a current parameter.

Figure 10:
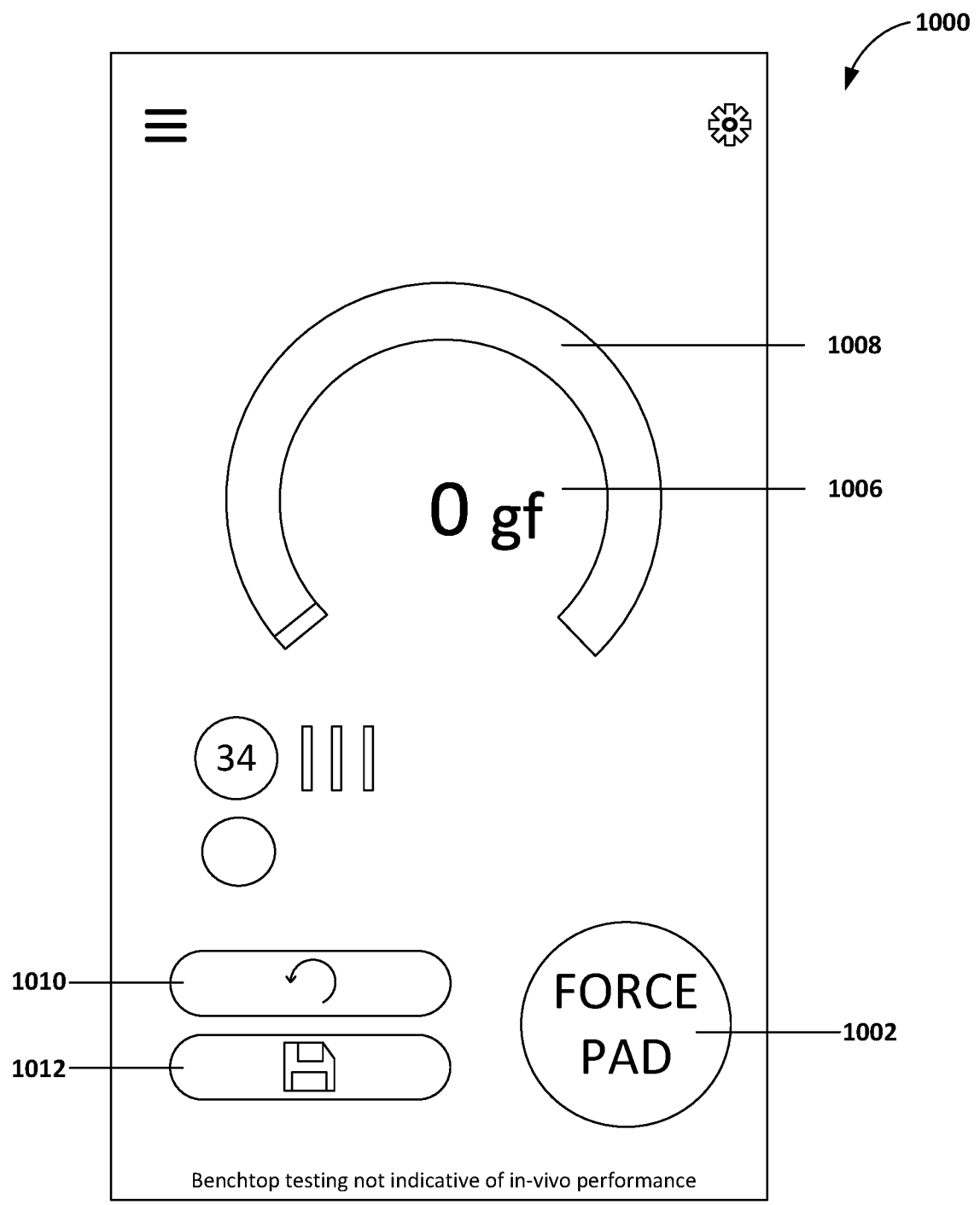
FIGS. 10 and 11A-11C illustrate example GUIs that may be generated and displayed by a computing device of any of the systems described herein.

FIG. 10 is another example GUI 1000 that may be generated by processing circuitry 226 and displayed on touchscreen 216 of computing device 218. GUI 1000 may be configured to interact with system 300 of FIG. 6.

GUI 1000 includes input region 1002 and output region 1006. Input region 1002 graphically indicates an area of touchscreen 216 with which conductive element 214 can be aligned (FIG. 5). For example, a user may place base 304 of device 302 next to computing device 218 such that when conductive element 214 pivots into contact with touchscreen 216, conductive elements 214 contacts the portion of touchscreen 216 in which input region 1002 is displayed.

Output region 1006 includes an area configured to display an indication of a parameter based on an electrical signal indicating the amount of contact between the conductive element 214 and touchscreen 216 determined by processing circuitry 226. For example, processing circuitry 226 may determine an approximate magnitude of a compressive force based on an electrical signal generated by touchscreen 216 based on input received via input region 1002, and GUI 1000 may display the approximate magnitude as a numerical value within output region 1006. For example, GUI 1000 may display the numerical value of the compressive force in units of Newtons (N), Earth-gravities (g), or gram-force (gf) within output region 1006. In some examples, GUI 1000 may additionally or alternatively display the approximate magnitude graphically, such as with circular force meter 1008.

In examples in which computing device 218 is configured to determine the magnitude of the compressive force at which wire 212 begins to bend, GUI 1000 may include reset button 1010 and save button 1012, enabling a user to determine a new value of the magnitude, or store the currently determined value, respectively.

Figure 11C:
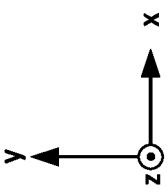
Figure 11C:
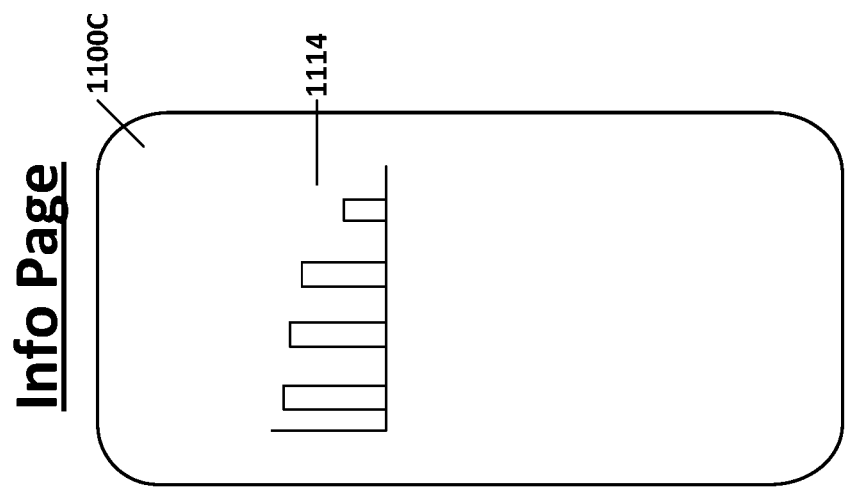
Figure 11B:
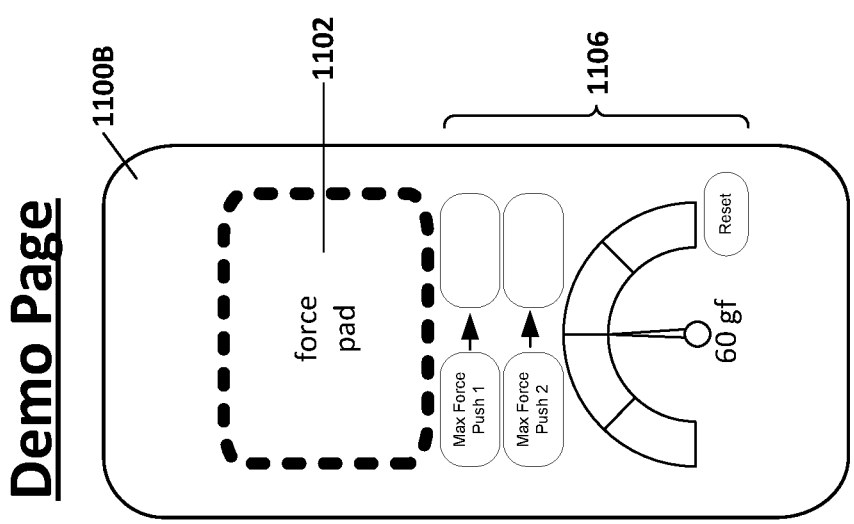
Figure 11A:
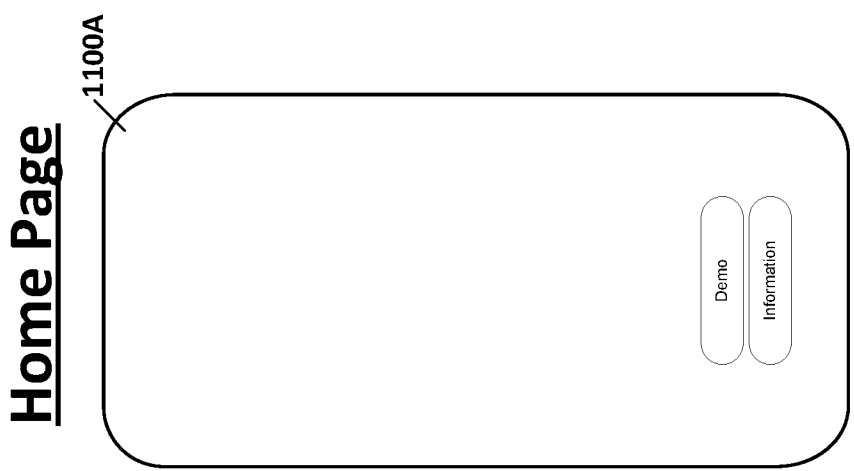

FIGS. 11A-11C are example GUIs 1100A, 1100B, and 1100C that may be generated by processing circuitry 226 and displayed on touchscreen 216 of computing device 218 in some examples. FIG. 11A depicts an example main "home" page 1100A that allows a user to select between a demonstration page (FIG. 11B) and an information page (FIG. 11C).

FIG. 11B depicts an example demonstration ("demo") page 1100B of a GUI. The demo page is a GUI display via which a user obtains data regarding the flexibility of an elongated medical device. For example, GUI 1100B may be GUI 900 (FIG. 9) or GUI 1000 (FIG. 10). GUI 1100B includes an input region 1102 and output region 1106. Input region 1102 defines a predetermined area with which a user may align conductive element 214 and in which touchscreen 216 may receive input indicative of a compressive force applied to wire 212. Output region 1106 is configured to display one or more parameters indicative of the amount of compressive force applied to wire 212, e.g., which processing circuitry 226 determines based on an amount contact between conductive element 214 and touchscreen 216. For example, output region 1106 may display an indication of the compressive force, as determined by computing device 218. The indication may include a numerical value, a graphical indication, or a qualitative indication, such as a respective color that changes as a function of the amount of contact between touchscreen 216 and conductive element 214.

FIG. 11C depicts an information ("info") page 1100C of a GUI. The information page is a GUI display enabling a user to view data acquired on demo page 1100B. For example, info page 1100C may display for comparing the determined force values acquired from multiple trials on demo page 1100B, which may be trials using the same medical device or different medical devices. In some examples, info page 1100C may be configured to display the determined force values for two or more similar elongated medical devices, such as two different wires 212. Info page 1100C may display the results for comparison as numerical values or as graphical representations, such as bar graph 1114.

Figure 12:
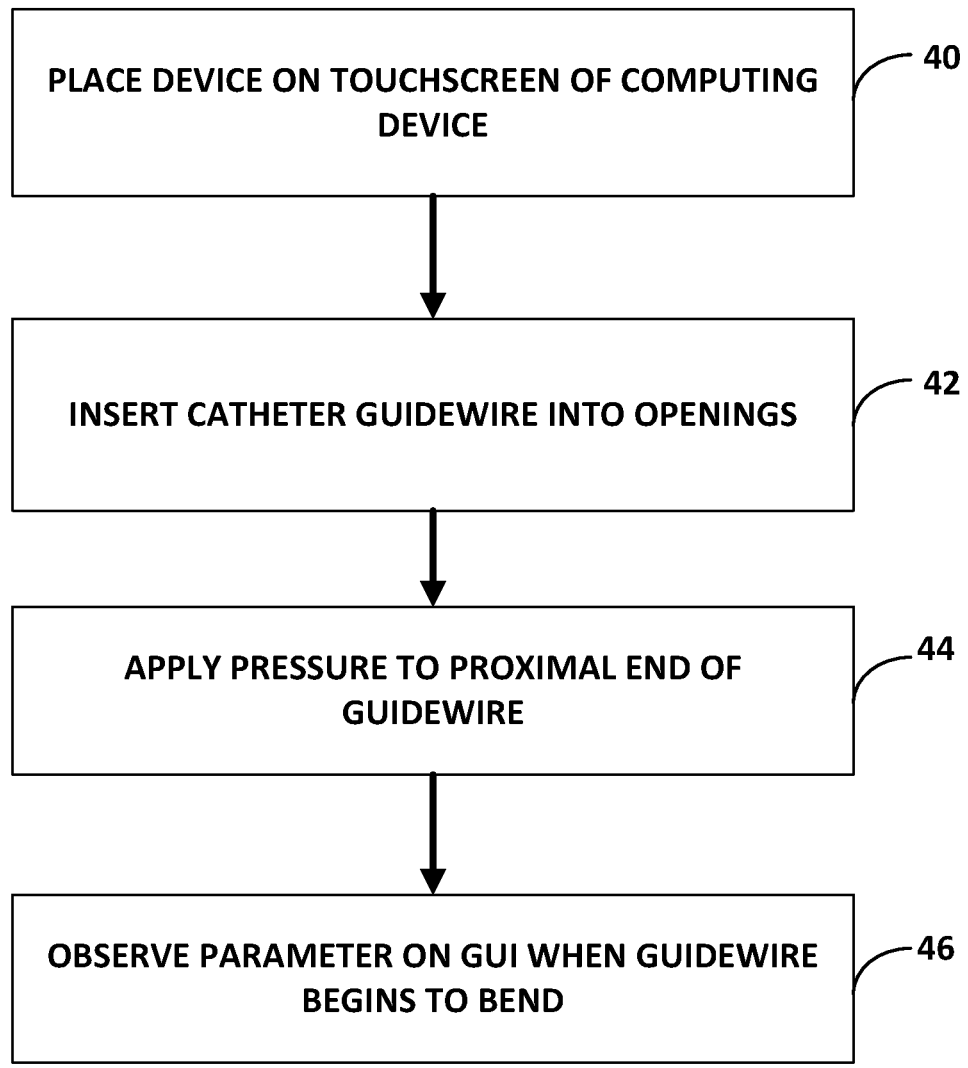
FIGS. 12-14 are flow diagrams of example methods of determining the flexibility of an elongated medical device.

FIG. 12 is a flow diagram depicting an example method of determining the integrity of an elongated medical device, such as via system 200 depicted in FIG. 2. User 224 places base 204 of body 232 of force-transmission device 202 onto touchscreen 216 of computing device 218 (40). User 224 inserts distal end 222 of wire 212 through arm opening 210 and into base opening 206, until distal end 222 contacts conductive element 214 (42). User 224 applies a compressive force, such as with a finger, to proximal end 220 of wire 212 or to a portion of wire 212 between proximal end 220 and arm 208 (44). Once user 224 has applied a sufficient compressive force, wire 212 will bend. Processing circuitry 226 of computing device 218 receives an indication (such as an electrical signal) of the amount of contact between conductive element 214 and touchscreen 216, and determines a parameter based on the indication, such as an approximate measurement of the magnitude of the compressive force. In some examples, processing circuitry 226 generates and presents a GUI (e.g., GUI 900 shown in FIG. 9 or GUI 1100B shown in FIG. 11B) that displays the parameter on touchscreen 216 for observation by user 224 (46).

Figure 13:
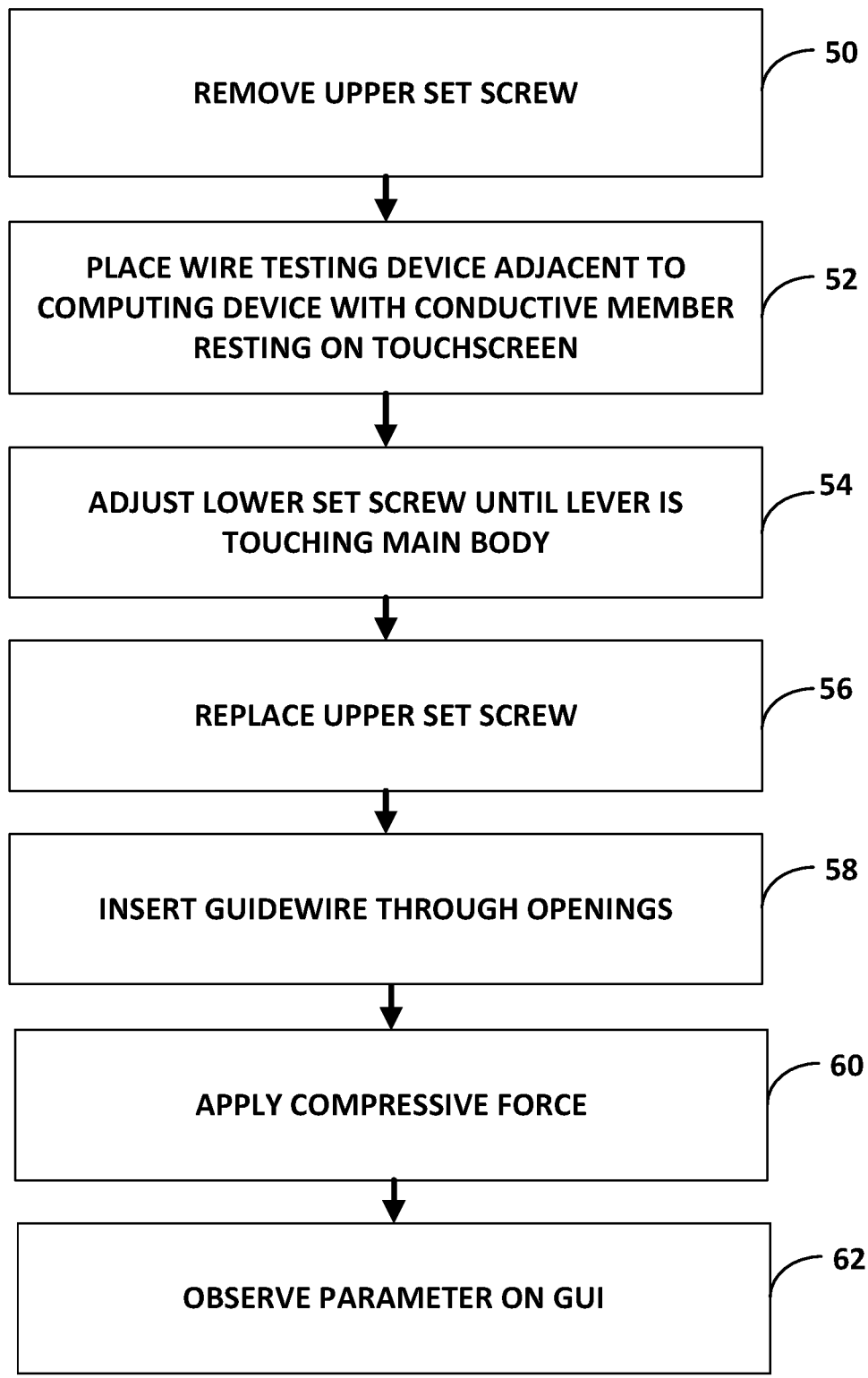

FIG. 13 is a flow diagram depicting an example method of determining the integrity of an elongated medical device, such as via system 300 depicted in FIG. 5. User 224 removes upper set screw 324 (50). User 224 places base 304 of device 302 adjacent to computing device 218, such that conductive element 214 is above touchscreen 216 (52). User 224 adjusts lower set screw 322 to a height at which conductive element 214 contacts touchscreen 216, and lever 320 contacts distal arm 308B at contact point 330 (54). User 224 inserts upper set screw 324 until upper set screw 324 contacts lower set screw 322 (56). User 224 inserts distal end 222 of wire 212 through proximal arm opening 310A and distal arm opening 310B, until distal end 222 contacts lever 320 (58). User 224 applies a compressive force, such as with one or more fingers, to proximal end 220 of wire 212 or to a portion of wire 212 between proximal end 220 and proximal arm 308A (60). Lever 320 rotates in response to the contact with wire 212, redirecting the force onto touchscreen 216. Once user 224 has applied a sufficient compressive force, wire 212 will bend, such as between proximal arm 308A and distal arm 308B (indicated in FIG. 7 by the thick black arrow pointing in the z-axis direction). Computing device 218 receives an indication (such as an electrical signal) of the compressive force via conductive element 214, and determines an approximate measurement of the magnitude of the compressive force based on the indication. In some examples, computing device may output the measurement via a GUI displayed on touchscreen 216, for observation by user 224 (62).

Figure 14:
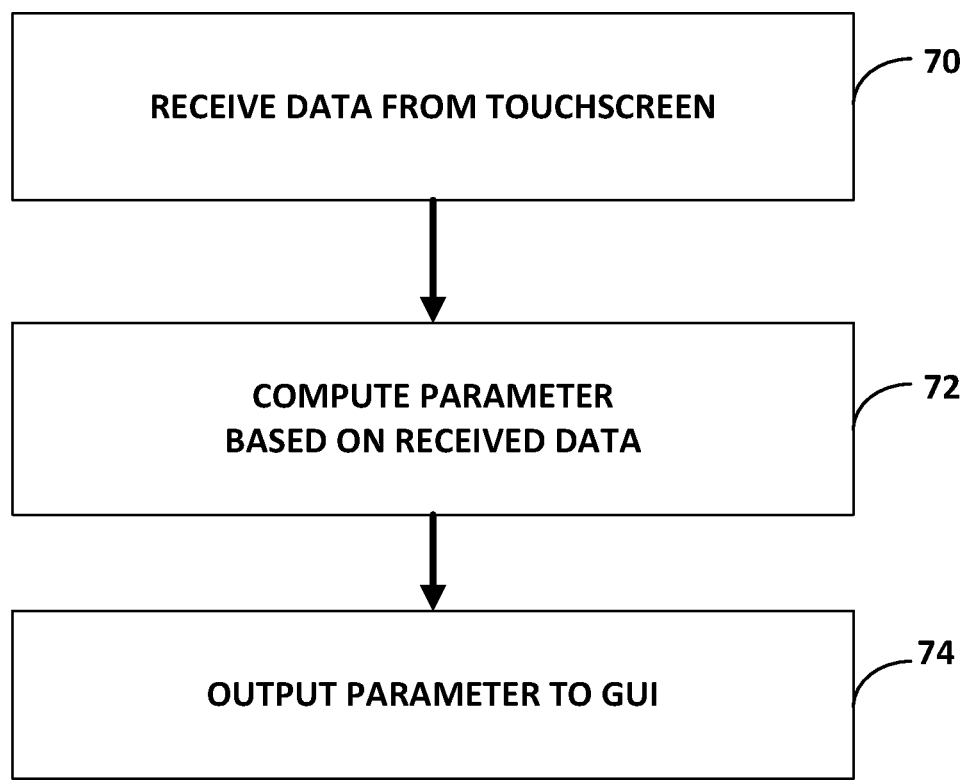

FIG. 14 is a flow diagram depicting a method of testing or measuring the flexibility of an elongated medical device. Although FIG. 14 is primarily described with reference to computing device 218, in other examples, processing circuitry of another computing device alone or in combination with computing device 218 may perform any part of the techniques described herein.

In the method of FIG. 14, processing circuitry 226 receives data from touchscreen 216, where the data may include an electrical signal that changes as a function of an amount of contact (such as an area of contact or an amount of force or pressure) between conductive element 214 and touchscreen 216, and, therefore, as a function of a compressive force applied to conductive element 214 by wire 212 (70). Other data from touchscreen 216 and received by processing circuitry 226 may indicate, for example, a location on the touchscreen.

Based on the received data, processing circuitry 226 determines a parameter, such as an approximate measurement of the magnitude of the compressive force applied to the wire (72). For example, computing device may compute a pre-determined algorithm relating the electrical signal to a magnitude of a compressive force. In another example, computing device 218 may retrieve, from a memory storage, an entry from a lookup table indicating a compressive force magnitude corresponding to the electrical signal.

In some examples, computing device 218 may be configured to monitor the signal received from the touchscreen and determine the point at which the corresponding compressive force stops increasing or otherwise changing, and store this value as the minimum compressive force required to cause the medical device to bend.

Computing device 218 may output the determined magnitude of the compressive force to a GUI for display on the touchscreen (74). For example, the GUI may display an indication of the compressive force as a numerical value, or as a graphical representation.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media, which includes any medium that facilitates transfer of a computer program from one place to another, e.g., per a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable storage medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if information is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by processing circuitry, e.g., one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A device comprising:
a body configured to receive an elongated medical device, wherein the elongated medical device is configured to be introduced into a patient; and
a conductive element configured to contact a touchscreen of a computing device, wherein an amount of contact between the conductive element and the touchscreen varies based on a compressive force applied to the elongated medical device when the elongated medical device is received within the body, wherein the body is configured to support and align the elongated medical device with respect to the conductive element; and
wherein the conductive element is pivotably connected to the body via a hinge.

2. The device of claim 1, wherein the body comprises:
a first body portion defining a first opening; and
a second body portion defining a second opening aligned with the first opening, wherein the first opening and the second opening are configured to receive the medical device.

3. The device of claim 2, wherein the first and second body portions are spaced apart from one another such that, in response to the compressive force, the medical device bends in a region between the first and second body portions.

4. The device of claim 1, wherein the conductive element comprises conductive silicone rubber.

5. The device of claim 1, wherein the amount of contact comprises at least one of a surface area between the touchscreen and the conductive element or an amount of force applied to the touchscreen by the conductive element.

6. A system comprising:
the device of claim 1; and
the computing device.

7. The system of claim 6, wherein the computing device comprises processing circuitry configured to:
receive input via the touchscreen, wherein the input indicates the amount of contact between the conductive element and the touchscreen,
determine a parameter based on the input, and
generate a graphical user interface indicating the determined parameter.

8. The system of claim 7, wherein the parameter comprises a magnitude of the compressive force applied to the conductive element via the elongated medical device when the elongated medical device is received within the body.

9. The system of claim 7, wherein the processing circuitry is configured to determine a minimum compressive force that causes the elongated medical device to bend based on an electrical signal generated by the touchscreen based on the amount of contact between the conductive element and the touchscreen.

10. The device of claim 1, wherein when the body receives the elongated medical device and before the compressive force is applied to the elongated medical device, the body is configured to hold a longitudinal axis of the elongated medical device substantially parallel or substantially perpendicular to a major surface of the touch screen.

11. A device comprising:
a body configured to receive an elongated medical device, wherein the elongated medical device is configured to be introduced into a patient; and
a conductive element configured to contact a touchscreen of a computing device, wherein an amount of contact between the conductive element and the touchscreen varies based on a compressive force applied to the elongated medical device when the elongated medical device is received within the body,
wherein the body comprises:
a first body portion defining a first through opening; and
a second body portion defining a second through opening, wherein the first through opening and the second through opening are aligned and configured to receive the medical device, and wherein a first part of the first body portion defining the first through opening is spaced from a second part of the second body portion defining the second through opening;
wherein the conductive element is pivotably connected to the body via a hinge.

12. The device of claim 11, wherein the first body portion comprises a first arm, the second body portion comprises a second arm, and the body further comprises a base between the first arm and the second arm.

13. The device of claim 11, wherein when the body receives the elongated medical device and before the compressive force is applied to the elongated medical device, the body is configured to hold a longitudinal axis of the elongated medical device substantially parallel or substantially perpendicular to a major surface of the touch screen.

14. The device of claim 11, wherein the body is configured to receive the medical device such that a distal end of the medical device engages a lever connected to the conductive element.

* * * * *